United States Patent [19]

Jonson

[11] Patent Number: 4,819,629

[45] Date of Patent: Apr. 11, 1989

[54] METHOD AND APPARATUS FOR DELIVERING AEROSOL TO THE AIRWAYS AND/OR LUNGS OF A PATIENT

[75] Inventor: Björn Jonson, Paris, France

[73] Assignee: Siemens Aktiengesellschaft, Berlin and Munich, Fed. Rep. of Germany

[21] Appl. No.: 110,449

[22] Filed: Oct. 20, 1987

[30] Foreign Application Priority Data

Oct. 28, 1986 [DE] Fed. Rep. of Germany ....... 3636669

[51] Int. Cl.$^4$ ............................................. A61M 15/08
[52] U.S. Cl. ........................... 128/203.22; 128/200.14; 128/204.23
[58] Field of Search ....................... 128/200.14, 200.23, 128/203.22, 203.29, 204.21, 205.24, 205.25

[56] References Cited

U.S. PATENT DOCUMENTS

| | | | |
|---|---|---|---|
| 3,923,056 | 12/1975 | Bingmann et al. | 128/204.21 |
| 3,991,304 | 11/1976 | Hillsman | 128/720 |
| 4,106,503 | 8/1978 | Rosenthal et al. | 128/145.6 |
| 4,186,737 | 2/1980 | Valenta et al. | 128/203.28 |
| 4,279,250 | 7/1981 | Valenta et al. | 128/200.14 |
| 4,340,044 | 7/1982 | Levy et al. | 128/204.21 |
| 4,462,398 | 7/1984 | Durkan et al. | 128/200.14 |
| 4,677,975 | 7/1987 | Edgar et al. | 128/200.14 |

FOREIGN PATENT DOCUMENTS

| | | |
|---|---|---|
| 0178925 | 10/1985 | European Pat. Off. . |
| 2346730 | 2/1980 | Fed. Rep. of Germany . |
| 2936433 | 6/1980 | Fed. Rep. of Germany . |

*Primary Examiner*—A. Michael Chambers

[57] ABSTRACT

A method and apparatus for delivering aerosol to the airways and/or lungs of a patient employ a separate inspiration line and expiration line connected to the patient, with an aerosol generator connected to the inspiration line. A respiration monitor is provided which generates signals corresponding to the breathing cycle of the patient, which is used to control the aerosol generator. Aerosol is generated during the expiration phase, and is deposited in the inspiration line. This permits adequate time to elapse before the aerosol is actually inhaled by the patient so that a stable droplet spectrum can be established. Moreover, a percisely controlled volume of respirator gas enriched with aerosol in the inspiration line can be supplied to the patient at exactly the proper point in time, independently of the flow volume.

20 Claims, 2 Drawing Sheets

METHOD AND APPARATUS FOR DELIVERING AEROSOL TO THE AIRWAYS AND/OR LUNGS OF A PATIENT

BACKGROUND OF THE INVENTION

1. Field of the Invention

The invention is directed to an apparatus for delivering aerosol to the airways and/or lungs of a patient, and to a method for operating such an apparatus.

2. Description of the Prior Art

In a great variety of ailments of the airways, a standard form of therapy is to supply pharmacologically active substances or water to the airways in aerosol form. The aerosol is generated in an aerosol generator as known, for example, from German Pat. No. 23 46 730 B2.

A known operating mode for arrangements for delivering aerosol is to activate the aerosol generator during the inspiration phase of the patient. Standard, so-called asthma atomizers operate in this way. The aerosol generation can be triggered by the patient or manually by a therapist, whereby an attempt is made to match the point in time of triggering to the inspiration of the patient. It is difficult to set the proper point in time and the proper dose in this manner. An additional problem is that the size of the aerosol droplets fluctuates greatly since they are often subject to a fast modification immediately after being generated. A designated delivery of aerosol to a defined location in the lungs or airways can thus not be reliably achieved.

Other arrangements operate with continuous aerosol generation during the entire respiratory cycle. During respirator treatment, such aerosol generation can disturb respiration under certain circumstances. Further, it is not possible to undertake the aerosol delivery only during a part of the inspiration, as is often desired, or to supply the aerosol only to a certain portion of the airways or lungs. Moreover, the aerosol forms deposits at undesired regions of the airways and/or lungs and only a small part of the frequently extremely expensive substances reach the desired regions in the respiratory tract.

In other known arrangements, the aerosol generator operates unsynchronized relative to the respiratory cycle and generates the aerosol in a container that is not connected to the airways during aerosol generation. The aerosol stored in the container is inhaled, by the patient after the container has been connected to the airways. Particularly in respiratory therapy, this operating mode is technologically complicated when identical quantities of aerosol are to be continuously inhaled or are to be inhaled with frequent repetition.

German Pat. No. 28 09 255 A1, corresponding to U.S. Pat. No. 4,106,503 discloses a dosing system for the aerosol delivery wherein the administration of aerosol ensues during a predetermined chronological duration of 0.1 through 1.0 seconds. The cooling of a thermistor due to the inhaled gas is used as control signal. The thermistor signal triggers the delivery of pressurized gas to an aerosol generator for the predetermined time. Subsequently, the patient ends the respiratory event with pure atmospheric air.

In another known arrangement (German No. 28 40 762 C3, corresponding to U.S. Pat. Nos. 4,186,737 and 4,279,250) for delivering aerosol to the respirtory tracts, a respirator having separate inspiration and expiration lines is connected to a patient. The aerosol generator discharges directly into stream of respiratory gas at the end of an inspiration phase and is again supplied by the atomizer of the inspiration line at the beginning of the next inspiration phase. The intended goal is that the aerosol is supplied during a brief time span in the first part of the inspiration phase.

In order to better set the suitable point in time for the aerosol delivery, a further known arrangement according to German Pat. No. 29 36 433 A1 provides that the aerosol generator is controlled by a signal linked to the control of the ventilation apparatus. The connection of the aerosol stream into the ventilation gas is controlled pressure-dependent or time-dependent. In accord with the desired distribution of the aerosol in the respiratory tract, the aerosol stream is added to the stream of respiratory gas either dependent on an inspiration pressure that has been reached or delayed relative to the beginning of the inspiration phase. To this end, the aerosol generator is connected to the inspiration line between ventilation apparatus and patient. A separate line is provided for the expiration. Further, the duration of the aerosol generation and thus the dose supplied, as well as the droplet size can be set for use in different regions of the respiratory tract. The productivity of the aerosol generator and its spectrum can be varied independently of the stream of respiratory gas.

The problem of precisely setting a suitable point in time in the respiratory cycle in order to selectively supply the desired region in the respiratory tract with aerosol still exists in all of these known arrangements. For example, the pressure in the airways is not always a reliable parameter for the quantity of respiratory gas already supplied. Resistances in the airways such as mucous or a cough on the part of the patient can lead to considerable increases in pressure. Further, the simple time delay at the beginning of the inspiration phase is not always a measure for the quantity of gas delivered. Morover, apart from the unsynchronized aerosol generation in a container which is not connected to the airways, the aerosol in the other arrangements is always generated immediately before inhalation by the patient. As already stated, the problem thus exists that the droplet size of the aerosol is subject to fast modifications and it is thus difficult to obtain a designated droplet size for treating specific regions of the respiratory tract.

SUMMARY OF THE INVENTION

The present invention has the object of improving an apparatus of the type described above such that designated aerosol delivery to selected regions of the respiratory tract is possible in a simple fashion while observing a selectable droplet spectrum. The arrangement should function independently of whether the patient is spontaneously breathing or is connected to a respirator for artificial or supportive ventilation of the airways and/or of the lungs.

The above objects are achieved in the present invention wherein, in contrast to the known arrangements, the aerosol in the is generated during the expiration phase and is deposited in the inspiration line. There is thus adequate time before the next inspiration phase so that a stable droplet spectrum can be established. Further, the proper volume of respiratory gas enriched with aerosol in the inspiration line can be supplied to the lungs and/or airways exactly at the proper point in time, regardless of how high the flow is and to which fluctuations it may possibly be subject.

The volume of delivered aerosol can be determined, for example, on the basis of the size of the inspiration line.

In one embodiment of the invention the aerosol is deposited in a predetermined region of the inspiration line. Tests have shown that no noteworthy mixing with the other regions ensues before the inspiration phase, so that the air column in the inspiration line enriched with aerosol proceeds into the respiratory tract as a defined air column during inhalation. It is possible to deliver aerosol volumes of different size to a patient with a larger volume of the inspiration line. In a structurally simple solution the aerosol generator can be connected to the inspiration line at valve-controlled lines can be provided for this purpose, respectively discharging into the inspiration line at different locations along said isspiration line.

Regardless of the type of aerosol generator employed, it is connected to a gas source via a valve, with the flow of the gas flowing through the aerosol generator being adjustable. To this end, the quantity of generated aerosol and the initially generated droplet size, and thus the droplet size established in stable fashion after a time, can be adjusted.

In a further embodiment of the invention the breathing rhythm of the patient is acquired with a flowmeter arranged in the inspiration and/or in the expiration line. It is thus possible to identify the breathing rhythm regardless of whether the patient is spontaneously breathing or is connected to a respirator. Additionally, the flow of respiratory gas during the inspiration phase can be adjustable. As a result, the enrichment of the aerosol in a defined region of the respiratory tract can be further improved. In particular, it is possible to undertake an intra-inspirational or post-inspirational pause. If a respirator is used, the flowmeter can be integrated therein.

In a further development of the invention a valve is arranged in the inspiration line between the patient and the connection of the aerosol generator. Thus the flow from the aerosol generator does not produce any additional air streams in the expiration line and, for example, can thereby not falsify the measurement of this flow.

DESCRIPTION OF THE PREFERRED EMBODIMENTS

Figure 1:
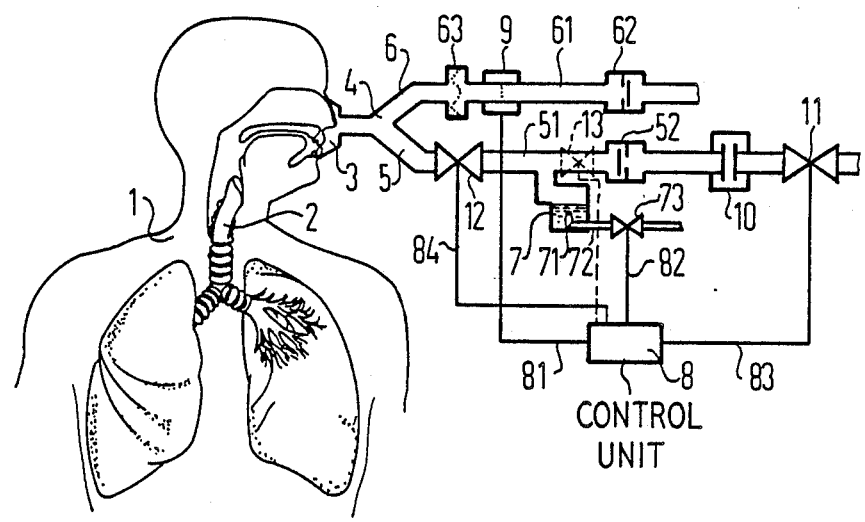
FIG. 1 is a schematic block diagram of a first embodiment of an aerosol supply system constructed in accordance with the principles of the present invention.

In FIG. 1, the airways 2 of a patient 1 are connected to a Y-section 4 via a breathing mask 3. A mouth piece, a trachial tube or some other suitable arrangement can be provided instead of the breathing mask. The Y-section 4 has a leg 5 for the connection of an inspiration line 51 and a leg 6 for an expiration line 61. The expiration line is provided with a check valve 62 which prevents the patient from inhaling via this line. Given spontaneous breathing, for example, the expiration line can be omitted and a check valve can be directly connected to the leg 6 of the Y-section 4. A filter 63 which prevents aerosol from proceeding into the environment via the expiration line 61 is also arranged in the line 61. The inspiration line 51 can be composed of a hose or of some other hollow member. The output of an aerosol generator 7 is connected to the line. Any suitable type of aerosol generator employed can be selected. By way of example, FIG. 1 shows a generator wherein gas flows out from a nozzle 71 and entrains fluid droplets. The aerosol generator 7 is connected to a gas source (not shown) via a line 72 through a valve 73. The valve 73 can be electrically or pneumatically controlled. When the valve 73 is open, aerosol is conducted from the generator 7 to the inspiration line 51. Given a closed valve 73 the delivery of aerosol to the inspiration line 51 is interrupted. Given the type of aerosol generator shown, the generation of aerosol likewise ceases. The valve 73 is controlled via a control unit 8 which, for example, operates electronically. This control unit 8 is supplied with signals identifying the phase in the respiratory cycle via the line 81, i.e., whether there is inspiration or expiration or a pause therebetween. In the present exemplary embodiment, wherein it is assumed that the patient is spontaneously breathing, these signals are generated by a flowmeter 9 which is arranged in the expiration line 61.

The control unit 8 contains means which generate an opening signal to the valve 73 via the line 82, after the expiration phase has begun, in a known manner with or without delay. The control unit 8 further contains adjustment means for adjusting the open duration of the valve 73. As needed, the control unit 8 can further be provided with means for regulating the flow of the gas through the valve 73, for example by changing the aperture cross-section of the valve 73. The open time of the valve 73 shall be referenced "To" below.

A check valve 52 which prevents gas and/or aerosol from flowing opposite the inspiration direction and thus emerging from the overall arrangement is also provided in the inspiration line 51. The inspiration line is also provided with an adjustment element 10 for the gas flow in this line and a valve 11 which receives control signals from the control device 8 via a line 83. The check valve 52, the adjustment element 10 for the flow and the valve 11 may be omitted without departing from the principles of the present invention.

A further valve 12 which also receives control signals from the control unit 8 via a line 84 is provided in the inspiration line 51 between the leg 5 of the Y-section 4 and the connection of the aerosol generator 7 to the inspiration line 51. By variation and selection of a number of parameters of the system, this embodiment permits, after inhalation, the inhaled aerosol to be deposited with the greatest possible precision within that section or region of the airways from the mouth or nose to the alveolae needed for every application.

The size of the generated droplets can be set within a narrow spectrum the selection of the aerosol generator and by adjusting its operation such as, for example, the amount and/or the rate of the gas conducted therethrough. It is known that the location at which the aerosol collects in the airways is at least partially dependent on the size of the droplets. On the basis of a combination of the gas flow through the line 72, of the open time "To" of the valve 73 and of the available volume "V51" of the inspiration line 51, it can be achieved within certain limits that the aerosol is deposited in a defined region of the airways and/or lungs. When setting this combination, the known or estimated size of the volume "Vt" of a breath as well as the siz of the volume "Vd" of the airway from mouth or nose down to the level at which the deposition of the aerosol is provided.

When there is a desire for the aerosol to be selectively deposited in the alveolae, the aerosol generator 7 is operated such that the size of the droplets is adequately small in order to penetrate into the level of the alveolae, but is not so small that a substantial part of these droplets is breathed out again at the following expiration. Further, the values for the gas flow are set by the line 72 and the open time "To" for the valve 73 so that the product of these two values roughly coincides with the volume "V51", so that the available volume of the inspiration line is completely filled with aerosol during the expiration phase. The volume "V51" can be selected such that the value is equal to or less than "Vt" minus "Vd".

In the exemplary embodiment of FIG. 1, for example, the valve 12 or the valve 13 (indicated with broken lines) is provided in the inspiration line. Both valves are in turn actuated by the control unit 8. By opening or closing these valves, the volume "V51" of the inspiration line can be varied in a simple fashion. For example, let it first be assumed that both valves are open and the full volume from the check valve 52 to the breathing mask 3 is filled with aerosol. The inhaled gas thus contains aerosol from the start and thus penetrates into the alveolae. Gas that does not extend to the alveolae but remains in the volume "Vd" is inhaled at the end of the inspiration phase. When the values of "Vt", "Vd", "To" and the gas flow through the line 72 are selected in the manner recited above, the respiratory gas no longer contains any aerosol in the final part of the inspiration phase. This reliably prevents aerosol, which would no longer reach the alveolae anyway from being wasted and more important, prevents a deposit of aerosol in the airways above the alveolae which would be more injurious than useful in certain circumstances.

When the aerosol is to be deposited in other regions of the respiratory tract, other combinations of the droplet size, the volume "V51", the gas flow through the aerosol generator and the time "To" are correspondingly selected. As an example, let it be assumed that "Vd" amounts to 75 ml; this means that the deposition of the aerosol should occur within an airway region that begins 75 ml below the breathing mask 3 and which, for example, extends from there about 100 ml into the airways. It is further assumed in this example that the overall volume of a breath "Vt" amounts to 500 ml. The following parameters are therefor selected in order to reliably prevent aerosol from penetrating further into the lungs, for example to the alveolae:

Flow×To=100 ml; V51=(500−75)=425 ml

First, the volume "V51" of the inspiration line is set to 425 ml in accord with the required value, such as with the indicated valves. Further, the 100 ml of the volume "V51" which are situated farthest from the patient are filled with aerosol during the inspiration phase. The 325 ml which are situated closer to the patient in the inspiration line thereby contain aerosol-free gas. In the following inspiration phase, 325 ml of aerosol-free gas are breathed in first. This volume reaches the peripheral parts of the lungs and airways in which no aerosol is to be deposited. The first 325 ml are followed by 100 ml with aerosol which therefor reach the region of the airways in which the deposition was desired. The last 75 ml of the breath are inhaled via the valve 11 and again contain aerosol-free respiratory gas, deposition of aerosol in this upper part of the airways being thereby avoided.

In the exemplary embodiment of FIG. 1, an adjustment element 10 for the flow of respiratory gas is also arranged in the inspiration line 51. Deposition of the aerosol can be controlled in a known way by controlling the flow during the inspiration. It is known that a high flow promotes the deposition in the upper regions of the airways and a low flow promotes the deposition in the more peripheral regions of the respiratory tract.

The valve 11 provided in the inspiration line 51 in the exemplary embodiment of FIG. 1 can be closed by a control pulse from the control unit 8 at a point in time when the aerosol has reached the region provided for deposition. This can usually occur at the conclusion of the inspiration phase and thereby corresponds to a controlled, post-inspiratcrial pause. However, it is also possible to provide an intra-inspiratorial pause which promotes the deposition of the aerosol in a defined portion of the airways to an even greater degree.

Figure 2:
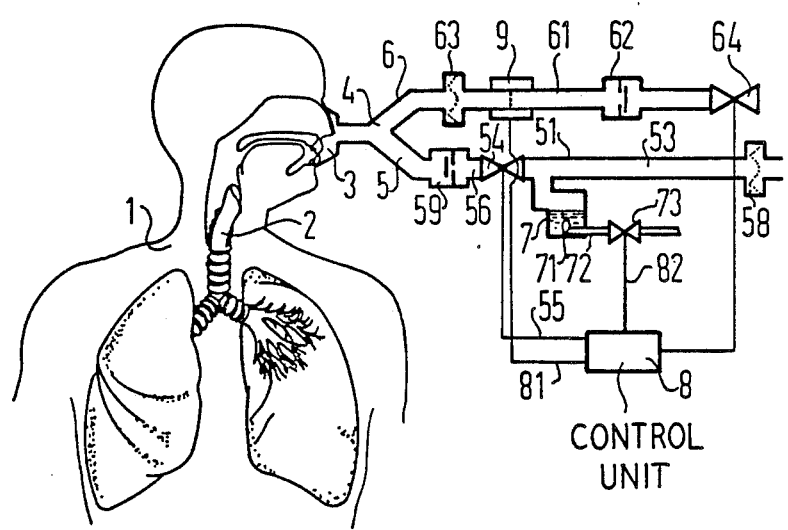
FIG. 2 is a schematic block diagram of a second embodiment of an aerosol supply system constructed in accordance with the principles of the present invention.

FIG. 2 shows a second embodiment. Identical parts are provided with the same reference characters as in FIG. 1. The aerosol is formed during the expiration phase while a solenoid valve 54 is closed. The aerosol is thus forced to flow against the flow direction of the inspiration gas and thus fills a cavity 53 having a volume selected to correspond to the size of the airway portion in which the aerosol is to be deposited. The cavity 53 is bounded by a filter 58 which prevents aerosol from proceeding into the environment. The filter 58 absorbs the excess of the aerosol, defined by flow×To, which exceeds the volume of the cavity 53. At the end of the expiration, which can again be indicated by the flowmeter 9, the valve 54 opens due to a signal supplied thereto from the control unit 8 via the line 55. A check valve 59 prevents a patient from exhaling through the line 51, for example given irregular breathing. During inspiration, the airways are thus initially supplied with a volume having aerosol-free gas, whereby the volume, except for that present in the leg 5 and the valve 59, is formed by a volume-adjutsable cavity 56, which is adjusted such that the aerosol-free volume of respiratory gas corresponds to a volume that is supplied to the deeper portions of the lung or airways during inspiration. The aerosol-free gas is then followed with aerosol-enriched gas which is in turn followed again by aerosol-free gas which is supplied via the filter 58.

Referring to the above example described in connection with FIG. 1, the volume of the cavity 56 is selected 325 ml together with the volume of the one-way valve 59 and of the leg 5. In this example, the volume of the cavity 53 amounts to 100 ml. The product of flow×To is selected such that it is equal to or greater than 100 ml.

This embodiment again allows the breathing of the patient to be controlled such that a post-inspiratorial phase occurs while the valve 54 and a corresponding valve 64 in the expiration line 61 are closed.

Figure 3:
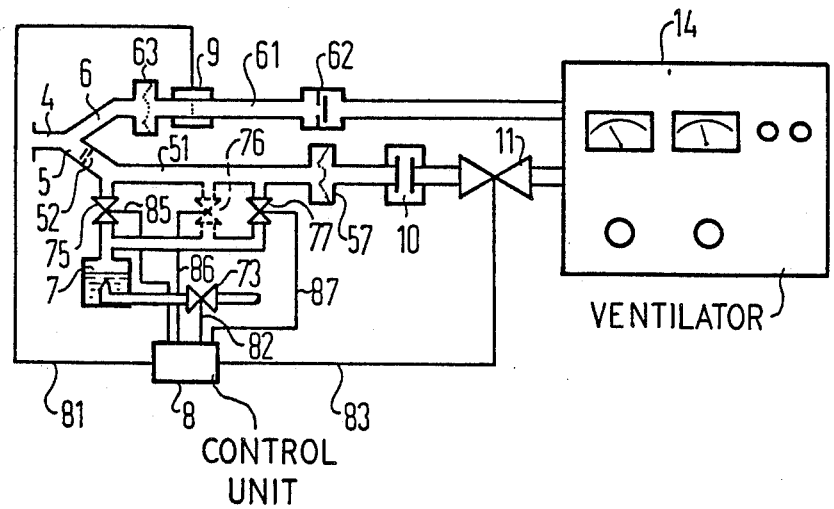
FIG. 3 is a schematic block diagram of a third embodiment of an aerosol supply system constructed in accordance with the principles of the present invention connected to a respirator.

FIG. 3 shows a further embodiment of the inventive arrangement for delivering aerosol which, by way of example, is connected to a respirator for artificial or supportive ventilation of the lungs. For simplicity, the patient has not been shown in FIG. 3. Identical parts are provided with the same reference characters.

In this exemplary embodiment, both the inspiration line 51 and the expiration line 61 are connected to a known respirator 14, for example, a servo-ventilator 900 C of Siemens Elema. The check valve 62 as well as the adjustment element for the flow 10 and the valve 11 can then be omitted under certain circumstances if they are component parts of the respirator 14. Further, an additional filter 57 is inserted into the inspiration line in this exemplary embodiment to prevent aerosol from proceeding into undesired spaces of the ventilation system. Differing from the exemplary embodiment of FIG. 1, the valve 52 for closing the inspiration line 51 is placed in the leg 5 of the Y-section 4. This is intended to prevent an undesired, additional gas stream from arising in the expiration line during the feed of aerosol from the aerosol generator 7 and thereby possibly falsifying the flow measurements.

The important difference in this exemplary embodiment, however, is that the aerosol generator 7 is connected to the inspiration line 51 via a plurality of lines, each provided with a valve 75 through 77 connected at different locations along the inspiration line 51. It is thereby possible to supply defined quantities of aerosol to selected regions (cavities) of the inspiration line 51 during the expiration phase. The valves 75 through 77 can again be actuated via the control unit 8 and via lines 85 through 87. The overall volume of the inspiration line 51 which can be filled with aerosol in accord with the exemplary embodiment of FIG. 2 corresponds to the volume between the valve 52 and the filter 57.

Although modifications and changes may be suggested by those skilled in the art it is the intention of the inventor to embody within the patent warranted hereon all changes and modifications as reasonably and properly come within the scope of his contribution to the art.

I claim as my invention:

1. An apparatus for delivering aerosol to the airways and/or lungs of a patient, comprising:
    an inspiration line and a separate expiration line connected to said patient;
    an aerosol generator connected to said inspiration line;
    means for monitoring the respiration cycle of said patient and generating control signals corresponding thereto; and
    said aerosol generator being connected to said means for monitoring and being supplied with a control signal therefrom such, that said aerosol generator generates aerosol only during the expiration phase of said patient and deposits the generated aerosol in said inspiration line during said expiration phase.

2. An apparatus as claimed in claim 1, further comprising a cavity in said inspiration line and connected to said aerosol generator into which said aerosol generator deposits the generated aerosol.

3. An apparatus as claimed in claim 2, wherein said cavity has an adjustable volume.

4. An apparatus as claimed in claim 2, wherein said cavity is disposed in said inspiration line at a distance spaced from said airways of said patient.

5. An apparatus as claimed in claim 2, further comprising an aerosol filter connected in said inspiration line between said cavity and the environment.

6. An apparatus as claimed in claim 1 further comprising:
    a cavity disposed in said inspiration line into said aerosol is deposited by said aerosol generator, said cavity being disposed in said inspiration line with a portion of said inspiration line extending between said cavity and said patient; and
    a valve disposed between said cavity and said portion of said inspiration, said valve being connected to said means for monitoring and being controlled thereby such that said valve is closed during the expiration phase of said patient.

7. An apparatus as claimed in claim 2, further comprising a check valve disposed in said inspiration line between said cavity and said patient which permits gas flow only in a direction toward said patient.

8. An apparatus as claimed in claim 7, wherein said check valve opens to permit gas flow therethrough at a predetermined pressure.

9. An apparatus as claimed in claim 8, further comprising a further check valve disposed in said expiration line permitting gas flow only in a direction away from said patient, said further check valve opening at a further predetermined pressure, said further predetermined pressure for said further check valve being less than the predetermined pressure for said check valve in said inspiration line.

10. An apparatus as claimed in claim 1, further comprising a plurality of lines connecting said aerosol generator to said inspiration line at respectively different locations of said inspiration line, each of said plurality of lines having a valve therein which controls flow of gas through the line, each valve in each line being connected to said means for monitoring and being chronologically controlled thereby.

11. An apparatus as claimed in claim 1 for use with a gas source, and further comprising a valve connected between said aerosol generator and said gas source, and to said means for monitoring for control thereby, such that said means for monitoring controls said valve to regulate the flow of gas through said aerosol generator.

12. An apparatus as claimed in claim 11, wherein said means for monitoring regulates the duration during which gas flows through said aerosol generator.

13. An apparatus as claimed in claim 1, wherein said means for monitoring includes a flowmeter disposed in said inspiration line for acquiring the respiration rhythm of said patient.

14. An apparatus as claimed in claim 1, wherein said means for monitoring includes a flowmeter disposed in said expiration line for acquiring the respiration rhythm of said patient.

15. An apparatus as claimed in claim 1, wherein said means for monitoring includes means for adjusting the flow of respiratory gas during the inspiration phase of said patient.

16. An apparatus as claimed in claim 15, wherein said means for adjusting the flow of regulatory gas includes means for interrupting the flow of respiratory gas to said patient at a predetermined point in time and for a predetermined duration.

17. An apparatus as claimed in claim 1, further comprising a respirator connected to said inspiration and expiration lines for artificial or supportive ventilation of said patient.

18. A method for supplying aerosol to the airways and/or lungs of a patient comprising the steps of:
    monitoring the respiration rhythym of said patient and generating control signals corresponding thereto;
    generating aerosol based on said control signals only during the expiration phase of said patient; and depositing the generated aerosol in an inspiration line connected to said patient during said expiration phase.

19. A method as claimed in claim 18, wherein said aerosol is generated in an aerosol generator, and comprising the additional step of regulating the duration during which gas flows through said aerosol generator.

20. A method as claimed in claim 18, comprising the additional step of regulating the flow of respiration gas during the inspiration phase of said patient.

* * * * *